(12) United States Patent
Tanimoto et al.

(10) Patent No.: US 7,850,928 B2
(45) Date of Patent: Dec. 14, 2010

(54) FIXED-BED SHELL-AND-TUBE REACTOR AND ITS USAGE

(75) Inventors: Michio Tanimoto, Himeji (JP); Hideto Hashiba, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 1075 days.

(21) Appl. No.: 11/409,588

(22) Filed: Apr. 23, 2006

(65) Prior Publication Data

US 2006/0245992 A1    Nov. 2, 2006

Related U.S. Application Data

(62) Division of application No. 10/040,671, filed on Jan. 6, 2002, now abandoned.

(30) Foreign Application Priority Data

Jan. 25, 2001    (JP) .............................. 2001-017064

(51) Int. Cl.
*F28D 7/16* (2006.01)
*B65G 69/00* (2006.01)

(52) U.S. Cl. .................. 422/201; 414/21; 549/239; 549/248; 549/257; 549/259; 549/534; 562/535; 562/564; 562/549; 568/479

(58) Field of Classification Search .................. 414/21; 422/201

See application file for complete search history.

(56) References Cited

U.S. PATENT DOCUMENTS

| | | | |
|---|---|---|---|
| 3,801,634 A | 4/1974 | Krabetz et al. | |
| 4,077,530 A | 3/1978 | Fukusen et al. | |
| RE29,901 E | 2/1979 | Wada et al. | |
| 4,402,349 A | 9/1983 | Engert et al. | |
| 4,461,327 A | 7/1984 | Magin et al. | |
| 4,537,874 A | 8/1985 | Sato et al. | |
| 4,707,460 A | 11/1987 | Ishii et al. | |
| 4,760,153 A | 7/1988 | Takahashi et al. | |
| 4,812,437 A | 3/1989 | Nojiri et al. | |
| 4,837,360 A | 6/1989 | Kadowaki et al. | |
| 5,145,824 A | 9/1992 | Buffum et al. | |
| 5,169,820 A | 12/1992 | Ueda et al. | |
| 5,198,581 A | 3/1993 | Kawajiri et al. | |
| 5,264,627 A | 11/1993 | Tazaki et al. | |
| 5,395,812 A | 3/1995 | Nagase et al. | |
| 5,504,052 A | 4/1996 | Rizkalla et al. | |
| 5,719,318 A | 2/1998 | Kawajiri et al. | |
| 5,959,124 A | 9/1999 | Hashiba et al. | |
| 5,959,143 A | 9/1999 | Sugi et al. | |
| 5,994,580 A | 11/1999 | Takahashi et al. | |
| 6,060,422 A | 5/2000 | Takahashi et al. | |
| 6,808,689 B1 | 10/2004 | Matsumoto et al. | |

FOREIGN PATENT DOCUMENTS

| CA | 2114681 A1 | 8/1994 |
|---|---|---|
| CN | 1003353 B | 2/1989 |
| CN | 1049368 C | 2/2000 |
| EP | 0 043 100 B2 | 1/1982 |
| EP | 0 207 550 B1 | 1/1987 |
| EP | 0 304 867 A2 | 3/1989 |
| EP | 0 608 837 B1 | 8/1994 |
| GB | 1 330 074 | 9/1973 |
| GB | 1 390 271 | 4/1975 |
| GB | 1 416 099 | 12/1975 |
| GB | 1 444 659 | 8/1976 |
| GB | 1 496 832 | 1/1978 |
| GB | 1 566 882 | 5/1980 |
| JP | 49-11371 | 3/1974 |
| JP | 50-13308 B | 2/1975 |
| JP | 50-35088 | 4/1975 |
| JP | 52-3579 | 1/1977 |
| JP | 52-85091 | 7/1977 |
| JP | 53-30688 | 8/1978 |
| JP | 55-67325 A | 5/1980 |
| JP | 56-23969 B2 | 6/1981 |
| JP | 56-52013 B2 | 12/1981 |
| JP | 57-21928 | 2/1982 |
| JP | 58-15176 | 3/1983 |
| JP | 59-12758 A | 1/1984 |
| JP | 59-76541 | 5/1984 |
| JP | 59-139923 A | 8/1984 |
| JP | 60-33539 B2 | 8/1985 |
| JP | 62-78 A | 1/1987 |
| JP | 62-4444 A | 1/1987 |
| JP | 62-30545 A | 2/1987 |
| JP | 63-116743 | 5/1988 |
| JP | 63-38331 B2 | 7/1988 |
| JP | 64-33162 U | 3/1989 |
| JP | 64-56634 A | 3/1989 |
| JP | 1-33152 Y2 | 10/1989 |
| JP | 3-9770 B2 | 2/1991 |
| JP | 3-26101 B2 | 4/1991 |
| JP | 4-217932 A | 8/1992 |
| JP | 5-84440 A | 4/1993 |
| JP | 5-115783 A | 5/1993 |
| JP | 5-279269 A | 10/1993 |
| JP | 5-329368 A | 12/1993 |
| JP | 6-279030 A | 10/1994 |
| JP | 7-10802 A | 1/1995 |
| JP | 7-51573 A | 2/1995 |
| JP | 7-29056 B2 | 4/1995 |
| JP | 8-299797 A | 11/1996 |

(Continued)

*Primary Examiner*—Bernard Dentz

(57) ABSTRACT

The present invention provides: a fixed-bed shell-and-tube reactor, which can stably produce an aimed product for a long period when a solid particulate material such as a catalyst is packed and used for each substance; and its usage. The fixed-bed shell-and-tube reactor comprises a plurality of reaction tubes that are packed with a solid particulate material and arranged in parallel, wherein the solid particulate material is weighed so as to be uniform volume, and is packed in each reaction tube in a packing time of not shorter than 30 seconds per liter.

15 Claims, No Drawings

FOREIGN PATENT DOCUMENTS

| JP | 9-241209 A | 9/1997 |
| JP | 9-316023 A | 12/1997 |
| JP | 10-57813 A | 3/1998 |
| JP | 10-120617 A | 5/1998 |
| JP | 10-167711 A | 6/1998 |
| JP | 10-510212 A | 10/1998 |
| JP | 11-333282 A | 12/1999 |

FIXED-BED SHELL-AND-TUBE REACTOR AND ITS USAGE

This is a divisional of U.S. patent application Ser. No. 10/040,671 filed Jan. 6, 2002 and claims the benefit thereof under 35 U.S.C. §120.

BACKGROUND OF THE INVENTION

A. Technical Field

The present invention relates to a fixed-bed shell-and-tube reactor in which a solid particulate material is packed, and its usage.

B. Background Art

A plenty of patent applications as to a process for packing a solid particulate material such as a catalyst into a fixed-bed shell-and-tube reactor have hitherto been filed. For example, the following processes are disclosed in JP-A-3579/1977 and JP-A-30545/1987 respectively: a process which involves inserting line steel from an upper opening of each reaction tube when a catalyst is packed, in a shell-and-tube reactor; and a process which involves flowing air from the bottom of a reaction tube when a pellet catalyst is packed in a shell-and-tube reactor. Furthermore, a process, which concerns a packing apparatus as used when a catalyst is packed in a shell-and-tube reactor, is disclosed in JP-A-67325/1980 and JP-A-21928/1982.

According to the above-mentioned conventional processes, the breakage and pulverization of the catalyst, which is caused when the catalyst is packed, is suppressed. Therefore, the desired catalyst-packing result can sufficiently be obtained. However, the improvement is further expected in order to stably produce an aimed product for a long period.

SUMMARY OF THE INVENTION

A. OBJECT OF THE INVENTION

Accordingly, an object of the present invention is to provide: a fixed-bed shell-and-tube reactor, which can stably produce an aimed product for a long period when a solid particulate material such as a catalyst is packed and used for producing each substance; and its usage.

B. DISCLOSURE OF THE INVENTION

In order to solve the above-mentioned problems, the present inventors diligently studied and performed experiments about a settled condition of packing a solid particulate material (especially, a catalyst) each in a plurality of reaction tubes in a fixed-bed shell-and-tube reactor (especially, the amount of a catalyst as packed in each reaction tube). As a result, they obtained the following findings and completed the present invention.

When a reaction gas is introduced into a shell-and-tube reactor in which a catalyst is packed and an aimed product is stably, produced for a long time, the number of reaction tubes generally reaches 3,000 to 30,000 in industrial scale operation using a fixed-bed shell-and-tube reactor. Then, it is ideally necessary that the amount of such as a catalyst packed in each reaction tube is uniform among the respective reaction tubes, and the pressure drop through a solid particulate material, such as a catalyst, of each reaction tube after packing the solid particulate material is uniform among the respective reaction tubes. However, when the packing is carried out in an industrial reactor, the amount of the catalyst as required for packing reaches scores of tons, and it is necessary to produce in two or more lots. When such a plenty of catalysts are produced, the catalysts as obtained have some differences as to physical various conditions, such as shape, size, and density among respective production lots. Therefore, when these are packed in the plurality of reaction tubes, the amount of the catalyst packed in each reaction tube and the pressure drop of each reaction tube is greatly varied, and it requires much time and labor to adjust the amount of the catalyst as packed (namely, the length of a layer of the packed catalyst) and the pressure drop.

Accordingly, a fixed-bed shell-and-tube reactor, according to the present invention, is a reactor, wherein a solid particulate material is weighed so as to be uniform volume, and is packed in each reaction tube in a packing time of not shorter than 30 seconds per liter.

A process for using a fixed-bed shell-and-tube reactor, according to the present invention, is to produce each substance by using the fixed-bed shell-and-tube reactor.

These and other objects and the advantages of the present invention will be more fully apparent from the following detailed disclosure.

DETAILED DESCRIPTION OF THE INVENTION

The solid particulate material as used in the present invention is not especially limited, but examples thereof include a catalyst and an inert substance.

The catalyst is not especially limited, and conventional ones can be used. Examples thereof include the following (1) to (10):

(1) a catalyst that comprises silver as an essential component, and is for a production of ethylene oxide by oxidizing ethylene in a gas phase (for example, JP-A-116743/1988, JP-A-4444/1987, JP-A-329368/1993, JP-A-510212/1998, and JP-A-84440/1993);

(2) a catalyst that comprises molybdenum, bismuth, and iron as essential components, and is for a production of (meth)acrolein and (meth)acrylic acid by oxidizing propylene, isobutylene, tert-butanol, and/or methyl tert-butyl ether in a gas phase (for example, JP-A-13308/1975, JP-A-56634/1989, JP-B-52013/1981, JP-B-23969/1981, and JP-A-76541/1984);

(3) a catalyst that comprises molybdenum and vanadium as essential components, and is for a production of acrylic acid by oxidizing acrolein in a gas phase (for example, JP-B-11371/1974, JP-A-85091/1977, JP-A-279030/1994, and JP-A-299797/1996);

(4) a catalyst that comprises molybdenum and phosphorus as essential components, and is for a production of methacrylic acid by oxidizing methacrolein in a gas phase (for example, JP-B-33539/1985, JP-B-26101/1991, and JP-A-12758/1984);

(5) a catalyst that comprises vanadium and titanium as essential components, and is for a production of phthalic anhydride by oxidizing o-xylene and/or naphthalene in a gas phase (for example, JP-B-29056/1995 and JP-B-15176/1983);

(6) a catalyst that comprises molybdenum as an essential component, and is for a production of maleic anhydride by oxidizing benzene in a gas phase (for example, JP-A-78/1987);

(7) a catalyst that comprises phosphorus and vanadium as essential components, and is for a production of maleic anhydride by oxidizing n-butane in a gas phase (for example, JP-A-167711/1998, JP-A-51573/1995, JP-A-115783/1993, and JP-A-35088/1975);

(8) a catalyst that comprises molybdenum as an essential component, and is for a production of propylene, acrolein, and/or acrylic acid by oxidizing propane in a gas phase (for example, JP-A-316023/1997, JP-A-57813/1998, and JP-A-120617/1998);

(9) a catalyst that comprises vanadium as an essential component, and is for a production of pyromellitic anhydride by oxidizing durene in a gas phase; and

(10) other solid particulate catalyst used for a gas-phase catalytic oxidation reaction by packing in a fixed-bed shell-and-tube reactor.

Incidentally, the catalyst, which is an example of the solid particulate material as used by packed in the fixed-bed shell-and-tube reactor according to the present invention, is not especially limited to the above solid particulate catalysts (1) to (10) used for a gas-phase catalytic oxidation reaction, but it also includes solid particulate catalysts used for such as an ammoxidation reaction, a hydrogenation reaction, and a dehydrogenation reaction.

The inert substance, for example, can be used as: a support material for supporting a catalyst; a catalyst-diluting agent; and a preheating or cooling material for a reaction gas when a catalyst is packed in a fixed-bed shell-and-tube reactor. It generally means an inert substance for the above oxidation reaction (a raw material and an aimed product). Examples thereof are not especially limited, but include silica, alumina, silica-alumina, and metals (for example, stainless). In addition, its shape is not especially limited, but examples thereof include a spherical shape, a ring shape, a raschig-ring shape, and a column shape.

The inert substance can be used either alone respectively or in combinations with each other.

The packing amount of the solid particulate material as packed in each reaction tube in the present invention can fitly be determined by using a reaction tube and carrying out a packing test, wherein the inner diameter and length of the reaction tube are the same as those of the reactor tube of the fixed-bed shell-and-tube reactor.

As to a process for uniformly packing the catalyst in each reaction tube of the fixed-bed shell-and-tube reactor, the following properties are considered: the packing amount obtained from the packing test; the density of the catalyst as used in the packing test (concretely, apparent density or bulk density); and each density of a catalyst group (production lot) comprising two or more catalyst-producing units. Then, the labor for adjusting the length of the packed catalyst layer and the pressure drop is greatly diminished by weighing the catalyst so as to be uniform volume wherein the catalyst is packed in each reaction tube of the fixed-bed shell-and-tube reactor.

In the present invention, the apparent density and bulk density of the solid particulate material (for example, a catalyst as a representative) can be determined according to the method as shown later.

The bulk density can be determined from the weight of a solid particulate material and the volume of a receptacle, wherein solid particulate material is packed in the receptacle of which inner volume is known.

In the present invention, a solid particulate material is packed in a cylinder having an inner diameter of 40 cm and a height of 40 cm, and the cylinder is placed on a rubber-made cushion material, and is dropped three times from a height of 5 cm. After a catalyst is further packed in a space that is made in an upper portion of the receptacle, the cylinder is further dropped in the above way, and the similar procedure is repeated until the space cannot be made in an upper portion of the receptacle. Thereafter, the weight of the catalyst as packed in the receptacle is measured. If the weight of the catalyst is X (g) at this time, the bulk density (g/cm$^3$) is determined according to the following equation: X/($20^2$×circular constant×40).

The measurement method for the apparent density of the solid particulate material is not especially limited, but examples thereof include the following two methods.

(1) While the temperature (T (° C.)) is kept constant, a specific gravity bottle is packed with a solid particulate material (weight: w (g)) as accurately weighed, and mercury is injected up to the mark of the specific gravity bottle. Thereafter, the weight of the mercury (weight: W (g)) is weighed. On the other hand, a specific gravity bottle is not packed with the solid particulate and mercury is injected thereto in the same way, and then the weight of the mercury (weight: W' (g)) is weighed. In addition, the volume of the solid particulate material as packed is v (cm$^3$). Then, the method is to determine the apparent density of the solid particulate material according to the following equation.

Apparent density of solid particulate material=$w/v$ wherein: v=(W'−W)/d (d: density of mercury at a temperature of T (° C.))

(2) The method is to calculate from the true density (g/cm$^3$) and the pore volume (cm$^3$/g) of a solid particulate material according to the following equation.

Apparent density=1/((1/true density)+pore volume)

Incidentally, the true density is measured with Auto Pycnometer 1320 (produced by Shimadzu Seisakusho Co., Ltd.) according to a pressure comparison method of equilibrium helium.

The pore volume per 1 g of the solid particulate material is measured with Auto Pore III 9420 (produced by Shimadzu Seisakusho Co., Ltd.) according to a mercury penetration method.

In the present invention, the necessary amount of the solid particulate material to be packed in each reaction tube in the above way is determined in consideration of its density. That is to say, the following are considered: the weight is controlled in consideration of the difference of the apparent density or the bulk density among each production lot so that the volume of the solid particulate material to be packed in each reaction tube will be uniform; and the packing time when the solid particulate material is packed in each reaction tube is not especially limited, but it should be controlled by the shape and size of the solid particulate material and the relationship between the size of the solid particulate material and the diameter of the reaction tube. Concretely, the packing time is adopted in the range of not shorter than 30 seconds, favorably 30 to 120 seconds, per 1 liter (hereinafter, the term "liter" is abbreviated to "L") of the solid particulate material. Accordingly, the nonuniformity of the pressure drop and the length of the layer of the packed solid particulate material layer can be inhibited wherein the nonuniformity is caused when the solid particulate material is packed.

If the pulverization or breakage of the solid particulate material, or the scatter or sublimation of a component in the solid particulate material is caused while the reaction is carried out for a long period, the pressure drop may be varied with the passage of time. However, the pressure drop caused by packing the solid particulate material becomes uniform among the respective reaction tubes in the fixed-bed shell-and-tube reactor in the present invention. Therefore, even if the reaction is carried out for a long period, the nonuniformity caused by the variation of the pressure drop among the respective reaction tubes can be inhibited.

Even if the two or more fixed-bed shell-and-tube reactors according to the present invention are arranged in parallel, the pressure drop among the respective fixed-bed shell-and-tube reactors can be controlled and the nonuniformity of the pressure drop among them can be inhibited, wherein the pressure drop may be caused when the solid particulate material is packed to each reactor.

In the fixed-bed shell-and-tube reactor according to the present invention, the volume and pressure drop of the solid particulate material packed in the respective reaction tubes can be uniform. Therefore, the amount of a reaction gas as introduced into each reaction tube can be uniform when the reaction gas is fed to the reactor.

In the case where the packing time per 1 L of the solid particulate material is shorter than 30 seconds, the bridge (space where the solid particulate material is not packed) is caused, and the nonuniformity of the length of the packed solid particulate material layer is caused, and the yield of the aimed product tends to decrease. On the other hand, in the case where the packing time per 1 L of the solid particulate material is longer than 120 seconds, it takes much operating time to pack the solid particulate material.

In the fixed-bed shell-and-tube reactor according to the present invention, it is favorable that the length of the packed solid particulate material layer in each reaction tube and the pressure drop of each reaction tube caused by packing the solid particulate material is settled so as to be uniform all over the reaction tubes. When the reaction is carried out in practical industrial scale, its favorable range is, for example, in the following way.

In the fixed-bed shell-and-tube reactor, the length of the packed solid particulate material layer in each reaction tube is in the range of 90 to 110% (within ±10% of the average value) of the average value (average length of the packed layer), more favorably 95 to 105% (within ±5% of the average value) so that the volume of the solid particulate material as packed in each reaction tube can be uniform. Particularly, an extraordinarily heated portion (hot spot portion) is formed in the packed solid particulate material layer under an exothermic reaction. When the distribution of the length of the packed layer among the reaction tubes is broad, the position of the hot spot portion is varied among the reaction tubes. Therefore, it is difficult to carry out a stable operation.

The pressure drop of each reaction tube caused by packing the solid particulate material is not especially limited, but it is favorably in the range of 85 to 115% (within ±15% of the average value) of the average value (average pressure drop), more favorably 92 to 108% (within ±8% of the average value). When the pressure drop is settled in this range, the high yield of the aimed product can stably be maintained for a long period. When the distribution of the pressure drop among the reaction tubes is broad, the amount of a reaction gas as introduced into each reaction tube is ununiform. Particularly, if the pulverization or breakage of the solid particulate material, or the scatter or sublimation of a component in the solid particulate material is caused while the reaction is carried out for a long period, the variation of the pressure drop is different among the reaction tubes. Therefore, as a result, there are disadvantages in that the yield of the aimed product is decreased and it is difficult to carry out a stable operation.

The average length of the packed solid particulate material layer and the average pressure drop can be calculated by measuring length of the solid particulate material layer and pressure drop as to all the reaction tubes of the fixed-bed shell-and-tube reactor. However, the length of the solid particulate material layer and pressure drop are measured in the reaction tubes equivalent to 5% of the entirety of the reaction tubes in the fixed-bed shell-and-tube reactor, and the resultant average values can be used as representative values.

In the present invention, the pressure drop after packing the solid particulate material means a pressure value at an upper portion of the reaction tube when a gas (for example, air or nitrogen) is introduced from the upper portion of the reaction tube with a constant flow amount in a state that the bottom of the reaction tube is open. The measurement condition is not especially limited, but the condition can fitly be determined in consideration of the flow amount per one reaction tube when it is practically used for the reaction. For example, in case of packing a solid particulate material for a production of acrylic acid by oxidizing propylene, the flow amount of the gas can be selected in the range of 10 to 100 liter/minute (under standard conditions) when the pressure drop is measured.

In the fixed-bed shell-and-tube reactor according to the present invention, it is favorable that one or more species of solid particulate materials having different activities are packed in an order of different activity so as to suppress or inhibit an extraordinarily heat (hot spot) in the packed solid particulate material layer. The method for packing in the above way is not especially limited, but examples of the method for preparing one or more species of catalysts having different activities material for oxidizing such as propylene include: a method which involves changing the amount and/or kind of such as alkali metal (JP-B-38331/1988); a method which involves diluting with a substance that is inert for reaction (JP-B-30688/1978); a method which involves changing an occupation volume of a catalyst (JP-A-217932/1992 and JP-A-241209/1997); and a method which involves changing a ratio for supporting a catalytically active substance (JP-A-10802/1995). These methods can be used either alone respectively or fitly in combinations of each other.

As to an operation method for packing the solid particulate material in the fixed-bed shell-and-tube reactor, conventional ones can be used. For example, the operation can effectively be carried out using packing machines disclosed in such as JP-Y2-33152/1989, JP-B-9770/1991, and JP-A-333282/1999.

The reaction tube of the fixed-bed shell-and-tube reactor as used has a circular cross sectional shape in general. In the present invention, the inner diameter of the reaction tube is defined as a tube diameter of the reaction tube. This tube diameter is not especially limited, but it is favorably in the range of 15 to 50 mm, more favorably 20 to 40 mm, still more favorably 22 to 38 mm. In the case where the tube diameter of the reaction tube is smaller than 15 mm, the number of reaction tubes is increased. Therefore, there are disadvantages in that the production cost of the reactor is high. In addition, in the case where the tube diameter of the reaction tube is larger than 50 mm, the heat accumulation is increased at the hot spot portion, and besides, in case of the worst, there are disadvantages in that the tendency is toward such as causing a runaway reaction.

As to the particle diameter of the solid particulate material, for example, when the solid particulate material has a spherical or cylindrical shape, the diameter thereof is defined as a particle diameter. When it has a ring shape, the outer diameter thereof is defined as a particle diameter. When it has an elliptic shape, the average value of the long diameter and the short diameter thereof is defined as a particle diameter.

The ratio of the particle diameter (d) of the solid particulate material and the tube diameter (D) of the reaction tube is not especially limited, but it is favorable in the range of 0.1/1 to 0.5/1, more favorably 0.12/1 to 0.45/1, still more favorably 0.15/1 to 0.40/1. In the case where the ratio is smaller than 0.1/1, as a result, there are disadvantages in that the tendency is toward decreasing the yield of the aimed product because successive reactions are increased. In addition, in the case where the ratio is larger than 0.5/1, there are disadvantages in that the contact efficiency of the solid particulate material and the reaction gas is lowered and the tendency is toward decreasing the yield of the aimed product.

EFFECTS AND ADVANTAGES OF THE INVENTION

In the fixed-bed shell-and-tube reactor according to the present invention, the volume and packing time of a solid particulate material as packed in each reaction tube are uniform. Therefore, the amount of the solid particulate material as packed in each reaction tube (for example, packed layer length and volume) is uniform, and the pressure drop of each reaction tube as caused by packing the solid particulate material is uniform. When the reactor is practically used for a reaction, the amount of a reaction gas introduced into each reaction tube can be uniform. Accordingly, even if the reaction is continued for a long period and the pressure drop varies, the pressure drop among the respective reaction tubes of the fixed-bed shell-and-tube reactor is kept uniform and an aimed product can stably be produced for a long period.

According to the process for using the fixed-bed shell-and-tube reactor, according to the present invention, each substance can be produced using the fixed-bed shell-and-tube reactor. Therefore, the aimed product can stably be produced for a long period.

DETAILED DESCRIPTION OF THE PREFERRED EMBODIMENTS

Hereinafter, the present invention is more specifically illustrated by the following examples and comparative examples. However, the present invention is not limited thereto. Incidentally, the conversion and yield are defined in the following way:

Conversion (mol %)=molar number of raw material as reacted/molar number of raw material as supplied×100

Yield (mol %)=molar number of aimed product as produced/molar number of raw material as supplied×100

REFERENTIAL EXAMPLE 1

(Preparation of Catalyst:)

First of all, 378 kg of cobalt nitrate, 172 kg of nickel nitrate, and 95 kg of iron (III) nitrate were dissolved in 500 L of ion-exchanged water. Separately, 138 kg of bismuth nitrate was dissolved in an aqueous nitric acid solution comprising 25 L of concentrated nitric acid and 100 L of ion-exchanged water. Further separately, 500 kg of ammonium paramolybdate was added to 1,500 L of heated ion-exchanged water to dissolve while being stirred. The resultant aqueous solution and the two aqueous solutions as prepared separately in the above way were drop-blended. Next, an aqueous solution, which was obtained by dissolving 2.4 kg of potassium nitrate in 50 L of ion-exchanged water, was added thereto.

The resultant slurry in the above way was heat-stirred and evaporated to dryness. Next, the resultant solid material was pulverized, and an adequate amount of ammonium nitrate and water as added to the resultant powder to knead them. Thereafter, the resultant kneaded material was molded into a ring shape having an outer diameter of 6 mm, an inner diameter of 2 mm, and a length of 1.1 times of the outer diameter, and then calcined at 480° C. for eight hours, thus obtaining 600 kg of a catalyst (1).

The composition of metal elements (except for oxygen, hereinafter in the same way) in this catalyst (1) was in the following way:

Catalyst (1):$Mo_{12}Bi_{1.2}Fe_1Co_{5.5}Ni_{2.5}K_{0.1}$

In addition, the apparent density of the catalyst (1) was 0.94 g/cm$^3$.

REFERENTIAL EXAMPLE 2

A catalyst (2) was obtained in the same way as of Referential Example 1 except that 2.4 kg of potassium nitrate was replaced with 3.2 kg of cesium nitrate and the outer diameter of the ring-molded product was changed to 8 mm.

The composition of metal elements in this catalyst (2) was in the following way:

Catalyst (1):$Mo_{12}Bi_{1.2}Fe_1Co_{5.5}Ni_{2.5}CS_{0.07}$

In addition, the bulk density of the catalyst (2) was 0.92 g/cm$^3$.

EXAMPLE 1

After 1 L of the catalyst (1) was packed in a reaction tube having an inner reaction-tube diameter of 25 mm and a length of 3,000 mm in a packing time of 60 seconds, the packed catalyst layer length and the pressure drop were measured. The results were listed in Table 1. Incidentally, when the pressure drop was measured, air was used in a flow amount of 30 L/minute (under standard conditions).

EXAMPLES 2 TO 5 AND COMPARATIVE EXAMPLE 1

The catalyst (1) was packed in the same way as of Example 1 except that the packing times were changed to each 15, 30, 45, 90, and 120 seconds per 1 L of the catalyst (1), and the packed catalyst layer length and the pressure drop were measured. The results were listed in Table 1.

TABLE 1

| | Packing time (second) | Packed layer length (mm) | Pressure drop (Pa) |
|---|---|---|---|
| Comparative Example 1 | 15 | 2,500 | 4,440 |
| Example 1 | 60 | 2,180 | 6,660 |
| Example 2 | 30 | 2,300 | 5,900 |
| Example 3 | 45 | 2,200 | 6,400 |
| Example 4 | 90 | 2,170 | 6,760 |
| Example 5 | 120 | 2,165 | 6,830 |

In case of the catalyst (1), the values of the packed layer length and pressure drop were almost stable in a packing time of not shorter than 45 seconds per 1 L.

The packing was carried out in the same way such that the packing time was changed except that a ceramic ball having an average particle diameter of 8 mmφ or the catalyst (2) was used instead of the catalyst (1) in Examples 1 to 5 and Comparative Example 1. Then, the values of the packed layer length and pressure drop were almost stable in a packing time of not shorter than 30 seconds per 1 L of the ceramic ball, or in a packing time of not shorter than 60 seconds per 1 L of the catalyst (2).

EXAMPLE 6

When a solid particulate material was packed in a fixed-bed shell-and-tube reactor comprising 15,000 reaction tubes (diameter of reaction tube: 25 mmφ, and length of reaction tube: 3,500 mm), a ceramic ball having an average particle diameter of 8 mmφ, the catalyst (2), and the catalyst (1) were packed in this order from the bottom of the reaction tubes, and the aimed packed layer length of these solid particulate materials was determined to each 200 mm, 800 mm, and 2,200 mm. Herein, the ceramic ball as used was commercially available, but its bulk density was 1.4 g/cm³. In addition, the necessary amount of the catalyst (1) and catalyst (2) was produced scores of times in order to pack in the fixed-bed shell-and-tube reactor according to the procedures described in Referential Examples 1 and 2. Then, the bulk density of the catalyst (1) and catalyst (2) as obtained then was each in the range of 0.94±0.05 g/cm³ and 0.92±0.06 g/cm³.

The packing test was carried out by using one reaction tube of which inner diameter and length were equal to those of the reaction tube of the fixed-bed shell-and-tube reactor. When the ceramic ball, the catalyst (2), and the catalyst (1) were packed in this order with a length of each 200 mm, 800 mm, and 2,200 mm, the amount of each solid particulate material as packed was each 118 g, 338 g, and 950 g. When the amount of each solid particulate material as packed in 15,000 reaction tubes in total was calculated, the difference of the bulk density among production lots was considered. For example, in case of the catalyst (1), 990 g of the catalyst (1) was weighed out (950 g×0.98/0.94=990 g) when the bulk density of the production lot used for the packing test was 0.94 g/cm³ and the bulk density of other one production lot was 0.98 g/cm³.

late material per one reaction tube was the same without considering the difference of the bulk density among the respective solid particulate materials.

The distribution of the packed layer length was in the range of ±14% relative to the average length of the packed layer, and the distribution of the pressure drop was in the range of ±21% relative to the average pressure drop.

Next, the oxidation reaction of the propylene was carried out in the same way as of Example 6. The results were listed in Table 2.

COMPARATIVE EXAMPLE 3

Three kinds of receptacles were prepared wherein the receptacles had volume per one reaction tube of each of the ceramic ball having an average particle diameter of 8 mmφ, the catalyst (2), and the catalyst (1) in Example 6. The amount of each solid particulate material as packed was prepared in volume for 15,000 reaction tubes in total.

Each solid particulate material was packed according to the procedure described in Example 6, and the packed layer length and pressure drop were measured. As a result, the distribution of the packed layer length was in the range of ±11% relative to the average length of the packed layer, and the distribution of the pressure drop was in the range of ±17% relative to the average pressure drop.

Next, the oxidation reaction of the propylene was carried out in the same way as of Example 6. The results were listed in Table 2.

TABLE 2

| | Initial stage | | | | | After 8,000 hours | | | | |
|---|---|---|---|---|---|---|---|---|---|---|
| | Deviation of pressure drop | Reaction temperature (° C.) | Conversion of propylene (mol %) | Yield of acrolein (mol %) | Yield of acrylic acid (mol %) | Deviation of pressure drop | Reaction temperature (° C.) | Conversion of propylene (mol %) | Yield of acrolein (mol %) | Yield of acrylic acid (mol %) |
| Example 6 | ±7% | 310 | 97.5 | 84.5 | 9.0 | ±8% | 315 | 97.6 | 85.4 | 8.2 |
| Comparative Example 2 | ±21% | 310 | 96.3 | 79.0 | 11.5 | ±33% | 342 | 97.1 | 75.2 | 14.5 |
| Comparative Example 3 | ±17% | 310 | 96.6 | 80.3 | 10.9 | ±23% | 337 | 96.9 | 77.3 | 13.2 |

After the ceramic ball, the catalyst (2), and the catalyst (1) were packed in this order in a packing time of each 45±5 seconds, 75±5 seconds, and 60±5 seconds, the packed layer length and pressure drop were measured. As a result, the distribution of the packed layer length was in the range of ±3% relative to the average length of the packed layer, and the distribution of the pressure drop was in the range of ±7% relative to the average pressure drop.

Into the reactor packed with the solid particulate material in the above way, a mixed gas, which comprised 8 volume % of propylene, 15 volume % of oxygen, 10 volume % of steam, and 67 volume % of an inert gas such as nitrogen, was introduced at a reaction temperature of 310° C., a contact time of 2.4 seconds, and a reactor-inlet pressure of 0.2 MPa (absolute pressure), and the oxidation reaction of the propylene was carried out. The results, which were obtained in the initial reaction stage and when 8,000 hours were passed, were listed in Table 2.

COMPARATIVE EXAMPLE 2

Each solid particulate material was packed in the same way as of Example 6 except that the weight of each solid particu-

REFERENTIAL EXAMPLE 3

(Adjustment of P-V Catalyst:)

In 400 L of isobutyl alcohol, 40 kg of vanadium pentoxide was suspended, and the resultant mixture was kept at 105° C. to carry out reduction for ten hours while being stirred. Separately, a phosphoric acid solution was prepared by dissolving 4.35 kg of orthophosphoric acid of 99 weight % in 100 L of isobutyl alcohol. When the phosphoric acid solution was added to the reduced vanadium solution and they were stirred for ten hours with heat-maintaining at 105° C., a dark blue precipitate was produced. After the reaction liquid slurry was left to cool, the produced precipitate was separated by filtration and was washed with acetone. Thereafter, the precipitate was dried at 140° C. for twelve hours. Then, the dried precipitate was molded into a cylindrical shape having a length of 5 mm and a diameter of 5 mm. Thereafter, the molded precipitate was calcined at 500° C. for four hours under a stream of air, thus obtaining 120 kg of a catalyst (3).

The composition of metal elements in this catalyst (3) was in the following way:

Catalyst (1):$P_{1.05}V_1$

In addition, the true density, the pore volume, and the apparent density of the catalyst (3) were 3.1 g/cm³, 0.38 cm³/g, and 1.42 g/cm³, respectively.

EXAMPLE 7

When the P-V catalyst was packed in a fixed-bed shell-and-tube reactor comprising 10,000 reaction tubes (diameter of reaction tube: 21 mmφ, and length of reaction tube: 3,000 mm), the aimed packed layer length of these solid particulate materials was determined to 2500 mm. The necessary amount of the catalyst (3) was produced scores of times in order to pack in the fixed-bed shell-and-tube reactor according to the procedures described in Referential Example 3. Then, the apparent density of the catalyst (3) as obtained then was in the range of 1.42±0.09 g/cm³.

The packing test was carried out by using one reaction tube of which inner diameter and length were equal to those of the reaction tube of the fixed-bed shell-and-tube reactor. When the catalyst (3) was packed with a length of 2500 mm, the amount of the catalyst (3) as packed was 796 g.

When the amount of each solid particulate material as packed in 10,000 reaction tubes in total was weighed out, the difference of the bulk density among production lots was considered. For example, 796 g of the catalyst (3) was weighed out (796 g×1.33/1.42=746 g) when the apparent density of the catalyst (3) of the production lot used for the packing test was 1.42 g/cm³ and the apparent density of other one production lot was 1.33 g/cm³.

After the catalyst (3) was packed in a packing time of 75±5 seconds per 1 L of the catalyst, the packed layer length and pressure drop were measured. As a result, the distribution of the packed layer length was in the range of ±2% relative to the average length of the packed layer, and the distribution of the pressure drop was in the range of ±5% relative to the average pressure drop.

Into the reactor packed with the catalyst (3) in the above way, an air-mixed gas, which comprised 1.8 volume % of n-butane, was introduced at a contact time of 3.6 seconds. Then, the reaction temperature was raised to 400 to 480° C. with a heating speed of 1° C./minute, and the activation treatment was carried out at 480° C. for twelve hours. Thereafter, an air-mixed gas comprising 1.8 volume % of n-butane was introduced at a contact time of 2 seconds, a reaction temperature of 380° C., and a reactor-inlet pressure of 0.18 MPa (absolute pressure), and the oxidation reaction of the n-butane was carried out. The results, which were obtained in the initial reaction stage and when 4,000 hours were passed, were listed in Table 3.

COMPARATIVE EXAMPLE 4

The catalyst (3) was packed in the same way as of Example 7 except that the weight as packed per one reaction tube was the same without considering the difference of the apparent density of the catalyst (3). The distribution of the packed layer length was in the range of ±21% relative to the average length of the packed layer, and the distribution of the pressure drop was in the range of ±17% relative to the average pressure drop.

Next, the oxidation reaction of the n-butane was carried out in the same way as of Example 7. The results were listed in Table 3.

TABLE 3

| | Initial stage | | | | After 4,000 hours | | | |
|---|---|---|---|---|---|---|---|---|
| | Deviation of pressure drop | Reaction temperature (° C.) | Conversion of n-C4 (mol %) | Yield of MAN (mol %) | Deviation of pressure drop | Reaction temperature (° C.) | Conversion of n-C4 (mol %) | Yield of MAN (mol %) |
| Example 7 | ±5% | 380 | 85.5 | 67.2 | ±7% | 375 | 85.5 | 65.0 |
| Comparative Example 4 | ±17% | 380 | 83.1 | 64.5 | ±20% | 375 | 82.9 | 60.0 | n-C4: n-Butane
MAN: Maleic anhydride

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for packing a fixed-bed shell-and-tube reactor with a solid particulate material, with the fixed-bed shell-and-tube reactor having a plurality of reaction tubes, with the process comprising the step of packing two or more production lots of said solid particulate material into said plurality of reaction tubes such that:
   a) each of said plurality of reaction tubes will have a pressure drop caused by the packing therein of said solid particulate material, wherein said pressure drop of each of said plurality of reaction tubes is in a range of 85 to 115% of an average pressure drop of said plurality of reaction tubes; and
   b) said solid particulate material packed in each of said plurality of reaction tubes will have a packed layer length being in a range of 90 to 110% of an average packed layer length of said solid particulate material packed in said plurality of reaction tubes;
   c) wherein said process further comprises the steps of:
      i) weighing out a predefined weight of said solid particulate material to be packed in each reaction tube of said fixed-bed shell-and-tube reactor such that said solid particulate material will have a uniform volume in each reaction tube of said fixed-bed shell-and-tube reactor, wherein said predefined weight of said solid particulate material to be packed in each reaction tube of said fixed-bed shell-and-tube reactor is determined by: determining a density of each of said production lots of said solid particulate material; carrying out a packing test using a reaction tube whose inner diameter and length are the same as those of the reaction tube of said fixed-bed shell-and-tube reactor to obtain a packing amount; and considering said packing amount and a difference between a density of a production lot of said solid particulate material as used in said packing test and a density of each of other production lots of said solid particulate material; and ii) packing said weighed-out predefined weight of said solid particulate material into each of said plurality of reaction tubes of said fixed-bed shell-and-tube reactor.

2. A process for packing a fixed-bed shell-and-tube reactor according to claim 1, wherein said packing step ii) for each of said plurality of reaction tubes of said fixed-bed shell-and-tube reactor is carried out in a time span of not shorter than 30 seconds per liter of said solid particulate material.

3. A process for packing a fixed-bed shell-and-tube reactor according to claim 1, wherein each of said plurality of reaction tubes has an inner diameter in a range of 15 to 50 mm.

4. A process for packing a fixed-bed shell-and-tube reactor according to claim 1, wherein said solid particulate material includes a plurality of particles, with each of the particles having a particle diameter, wherein each of said plurality of reaction tubes has an inner diameter, and wherein the ratio of said particle diameter of each particle to said inner diameter of each reaction tube is in a range of 0.1/1 to 0.5/1.

5. A process for packing a fixed-bed shell-and-tube reactor according to claim 1, wherein said packing step ii) for each of said plurality of reaction tubes of said fixed-bed shell-and-tube reactor is carried out in a time span of 30 to 120 seconds per liter of said solid particulate material.

6. A process for packing a fixed-bed shell-and-tube reactor according to claim 1, wherein said solid particulate material is at least one kind selected from the following groups (1) to (9):

(1) a catalyst that comprises silver as an essential component and is for a production of ethylene oxide by oxidizing ethylene in a gas phase;

(2) a catalyst that comprises molybdenum, bismuth, and iron as essential components and is for a production of (meth)acrolein and (meth)acrylic acid by oxidizing propylene, isobutylene, tert-butanol, and/or methyl tert-butyl ether in a gas phase;

(3) a catalyst that comprises molybdenum and vanadium as essential components and is for a production of acrylic acid by oxidizing acrolein in a gas phase;

(4) a catalyst that comprises molybdenum and phosphorus as essential components and is for a production of methacrylic acid by oxidizing methacrolein in a gas phase;

(5) a catalyst that comprises vanadium and titanium as essential components and is for a production of phthalic anhydride by oxidizing o-xylene and/or naphthalene in a gas phase;

(6) a catalyst that comprises molybdenum as an essential component and is for a production of maleic anhydride by oxidizing benzene in a gas phase;

(7) a catalyst that comprises phosphorus and vanadium as essential components and is for a production of maleic anhydride by oxidizing n-butane in a gas phase;

(8) a catalyst that comprises molybdenum as an essential component and is for a production of propylene, acrolein, and/or acrylic acid by oxidizing propane in a gas phase; and (9) a catalyst that comprises vanadium as an essential component and is for a production of pyromellitic anhydride by oxidizing durene in a gas phase.

7. A process for producing ethylene oxide, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes ethylene, and wherein the solid particulate material is a solid particulate catalyst which includes silver as an essential component; and thereafter oxidizing said ethylene in the presence of the solid particulate catalyst in a gas phase to thereby obtain ethylene oxide.

8. A process for producing (meth)acrolein and (meth)acrylic acid, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes propylene, isobutylene, tert-butanol, and/or methyl tert-butyl ether, and wherein the solid particulate material is a solid particulate catalyst which includes molybdenum, bismuth, and iron as essential components; and thereafter oxidizing said propylene, isobutylene, tert-butanol, and/or methyl tert-butyl ether in the presence of the solid particulate catalyst in a gas phase to thereby obtain (meth)acrolein and (meth)acrylic acid.

9. A process for producing acrylic acid, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes acrolein, and wherein the solid particulate material is a solid particulate catalyst which includes molybdenum and vanadium as essential components; and thereafter oxidizing said acrolein in the presence of the solid particulate catalyst in a gas phase to thereby obtain acrylic acid.

10. A process for producing methacrylic acid, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes methacrolein, and wherein the solid particulate material is a solid particulate catalyst which includes molybdenum and phosphorus as essential components; and thereafter oxidizing said methacrolein in the presence of the solid particulate catalyst in a gas phase to thereby obtain methacrylic acid.

11. A process for producing phthalic anhydride, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes o-xylene and/or naphthalene, and wherein the solid particulate material is a solid particulate catalyst which includes vanadium and titanium as essential components; and thereafter oxidizing said o-xylene and/or naphthalene in the presence of the solid particulate catalyst in a gas phase to thereby obtain phthalic anhydride.

12. A process for producing maleic anhydride, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes benzene, and wherein the solid particulate material is a solid particulate catalyst which includes molybdenum as an essential component; and thereafter oxidizing said benzene in the presence of the solid particulate catalyst in a gas phase to thereby obtain maleic anhydride.

13. A process for producing maleic anhydride, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes n-butane, and wherein the solid particulate material is a solid particulate catalyst which includes phosphorus and vanadium as essential components; and thereafter oxidizing said n-butane in the presence of the solid particulate catalyst in a gas phase to thereby obtain maleic anhydride.

14. A process for producing propylene, acrolein, and/or acrylic acid, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes propane, and wherein the solid particulate material is a solid particulate catalyst which includes molybdenum as an essential component; and thereafter oxidizing said propane in the presence of the solid particulate catalyst in a gas phase to thereby obtain propylene, acrolein, and/or acrylic acid.

15. A process for producing pyromellitic anhydride, comprising the steps of:

packing a solid particulate material into each of a plurality of reaction tubes of a fixed-bed shell-and-tube reactor by the process for packing a fixed-bed shell-and-tube reactor as recited in claim 1;

thereafter introducing an oxygen-containing reaction gas into each of said plurality of reaction tubes of the fixed-bed shell-and-tube reactor, wherein the oxygen-containing reaction gas includes durene, and wherein the solid particulate material is a solid particulate catalyst which includes vanadium as an essential component; and thereafter oxidizing said durene in the presence of the solid particulate catalyst in a gas phase to thereby obtain pyromellitic anhydride.

* * * * *